(12) United States Patent
Rele et al.

(10) Patent No.: US 7,476,753 B2
(45) Date of Patent: Jan. 13, 2009

(54) 3-ARYL-2-CYANO-3-HYDROXY-ACRYLIC ACID DERIVATIVES

(75) Inventors: Dinesh Narendra Rele, Mumbai (IN); Harjinder Singh Bhatti, Navi Mumbai (IN); Werner Hölzl, Eschentzwiller (FR); Sophie Marquais-Bienewald, Hegenheim (FR); Errol Vincent Mathias, Mumbai (IN); Andrea Preuss, Basel (CH); Barbara Wagner, Lörrach (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 86 days.

(21) Appl. No.: 10/565,789

(22) PCT Filed: Jul. 19, 2004

(86) PCT No.: PCT/EP2004/051533

§ 371 (c)(1),
(2), (4) Date: Jan. 25, 2006

(87) PCT Pub. No.: WO2005/012235

PCT Pub. Date: Feb. 10, 2005

(65) Prior Publication Data

US 2006/0228965 A1  Oct. 12, 2006

(30) Foreign Application Priority Data

Jul. 29, 2003 (EP) .................................. 03102324

(51) Int. Cl.
C07C 255/07 (2006.01)
A61K 8/34 (2006.01)

(52) U.S. Cl. ...................... 558/401; 424/401
(58) Field of Classification Search .................. 560/38; 558/401
See application file for complete search history.

(56) References Cited

U.S. PATENT DOCUMENTS 5,538,940 A * 7/1996 Sauter et al. ................ 504/314
5,686,228 A * 11/1997 Murray et al. .............. 430/350

OTHER PUBLICATIONS

Antimicrobial products in the home: The evolving problem of antibiotic resistance [online]; [retrieved on Jun. 16, 2008]; [URL;http://www.cps.ca/english/statements/ID/ID06-02.htm.*

XP-002266649, Database accession No. BRN 6212398, & BRN 6212566.
T. Kobayashi et al., Tetrahedron Letters, vol. 27, No. 39, pp. 4745-4748 (1986) and Abstract No. 107:58603.
Gazit et al., J. Med. Chem. vol. 34, (1991) pp. 1896-1907 and Abstract No. 115-8663.
Jalander, Synthetic Communications, vol. 23(16), (1993) pp. 2293-2302 and Abstract No. 120:244264.
Morel et al., Bulletin De La Societe Chimique De France No. 1-2, pp. 177-183 and Abstract No. 85:21548.
Saito et al., Synthesis (12), (Dec. 1982), pp. 1056-1059 and Abstract No. 98:125798.
English language abstract of CN 1 317 483, Abstract No. 138:89583.

* cited by examiner

Primary Examiner—Kamal A Saeed
Assistant Examiner—Shawquia Young
(74) Attorney, Agent, or Firm—Joseph C. Suhadolnik

(57) ABSTRACT

Disclosed are 3-aryl-2-cyano-3-hydroxy-acrylic acid derivates of formula(1a) (1b) or (1c) wherein $R_1$ is hydrogen, $C_1$-$C_{20}$alkyl; $C_1$-$C_{20}$alkoxy; $CF_3$; $C_6$-$C_{10}$aryl; or a radical of formula (1a) and $R_2$ is hydrogen; or $C_1$-$C_{20}$alkyl. The compounds are used as antimicrobial actives for the treatment of surfaces.

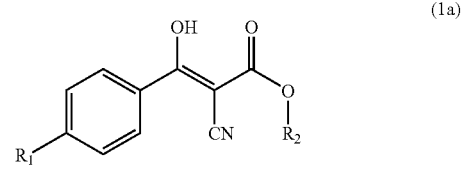

(1a)

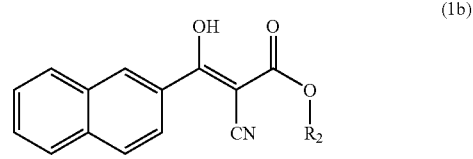

(1b)

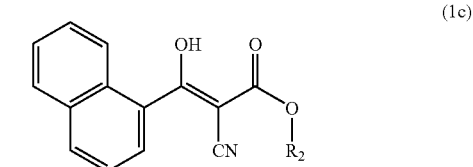

(1c)

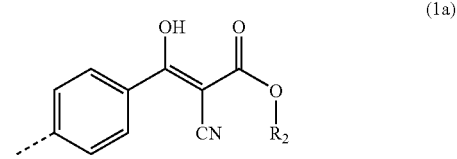

(1a)

8 Claims, No Drawings

3-ARYL-2-CYANO-3-HYDROXY-ACRYLIC ACID DERIVATIVES

The present invention relates to selected 3-aryl-2-cyano-3-hydroxy-acrylic acid derivatives, the preparation of these compounds, and to the use of such compounds for the antimicrobial treatment of surfaces, as antimicrobial active substances against gram-positive and gram-negative bacteria, yeasts and fungi and also for the preservation of cosmetics, household products, textiles and plastics and for use as disinfectants.

The present invention relates to 3-aryl-2-cyano-3-hydroxy-acrylic acid derivatives of formula

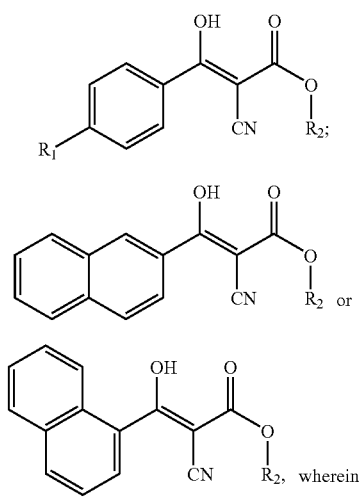

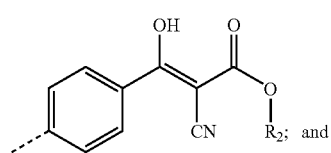

$R_1$ is hydrogen, $C_1$-$C_{20}$alkyl; $C_1$-$C_{20}$alkoxy; $CF_3$; $C_6$-$C_{10}$aryl; or a radical of formula (1a$_1$)

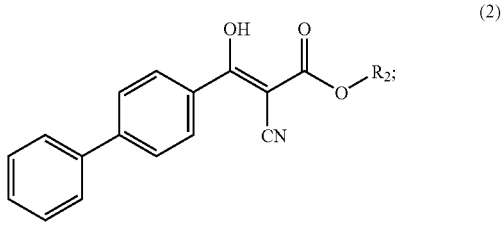

$R_2$ is hydrogen; or $C_1$-$C_{20}$alkyl.

$C_1$-$C_{20}$alkyl are straight-chain or branched alkyl radicals like methyl, ethyl, n-propyl, isopropyl, n-butyl, sec.butyl, tert.butyl, amyl, isoamyl or tert.amyl, hexyl, 2-ethylhexyl, heptyl, octyl, iso-octyl, nonyl, decyl, undecyl, dodecyl, tetradecyl, pentadecyl, hexadecyl, heptadecyl, octadecyl oder eicosyl.

$C_1$-$C_{20}$alkoxy are for example methoxy, ethoxy, n-propoxy, isopropoxy, n-butoxy, sek.butoxy, tert. butoxy, amyloxy, isoamyloxy oder tert.amyloxy, hexyloxy, heptyloxy, octyloxy, isooctyloxy, nonyloxy, decyloxy, undecyloxy, dodecyloxy, tetradecyloxy, pentadecyloxy, hexadecyloxy, heptadecyloxy oder octadecyloxy.

$C_6$-$C_{10}$aryl is for example naphthyl and preferably phenyl.

In accordance with the present invention, preference is given to compounds of formula (1a), wherein $R_1$ is $C_6$-$C_{10}$aryl, and most preferably phenyl.

Preference is given to compounds of formula (1a), (1b) or (1c), wherein $R_2$ is $C_1$-$C_{20}$-Alkyl.

Very special preference is given to compounds of formulae

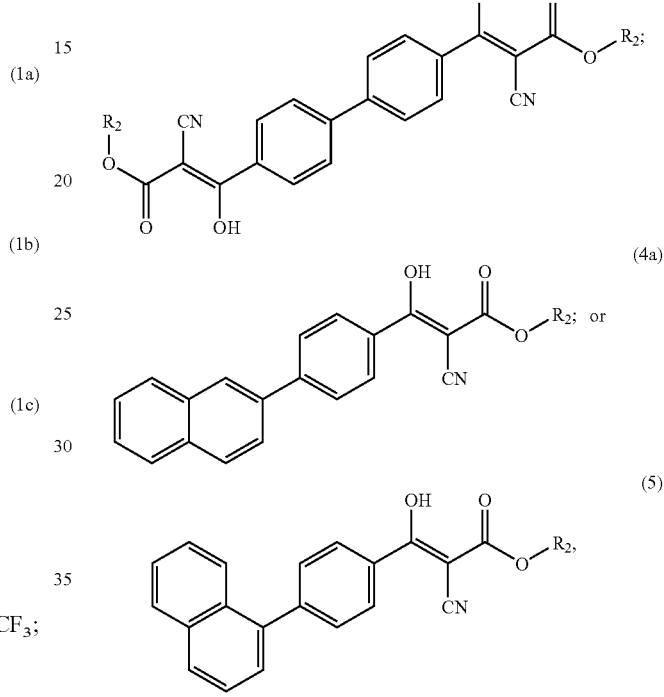

wherein in the formulas (2) to (5)

$R_2$ is $C_1$-$C_{20}$alkyl.

The preparation of the 3-aryl-2-cyano-3-hydroxy-acrylic acid derivatives can be carried out according to known methods.

For the preparation of the acrylic acid derivatives of the general formula (1a), (1b) or (1c) of the corresponding cyanoacetates of the formula (1d) are condensed with carbon acid chlorides of the formula (1c) at temperatures from −100° C. to +100° C., preferably at −80° C., in a suitable solvent, like diethylether or tetrahydrofuran in the presence of a base like metal alcoholates, metal silacides or metal amides, preferably lithium diisopropylamide according to the following reaction scheme:

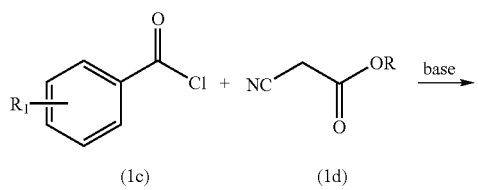

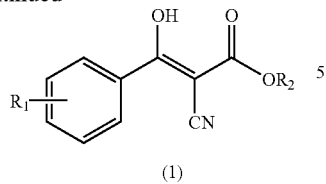

R$_1$ and R$_2$ are defined as given in formula (1a), (1b) or (1c).

The process for the preparation of the 3-aryl-2-cyano-3-hydroxy-acrylic acid derivates is a further object of the present invention.

The 3-aryl-2-cyano-3-hydroxy-acrylic acid derivatives of the present invention exhibit pronounced antimicrobial action, especially against pathogenic gram-positive and gram-negative bacteria and against bacteria of the skin flora, and also against yeasts and moulds. They are accordingly suitable especially for disinfection, deodorisation, and for general and antimicrobial treatment of the skin and mucosa and of integumentary appendages (hair), more especially for the disinfection of hands and wounds.

They are accordingly suitable as antimicrobial active substances and preservatives in personal care preparations such as, for example, shampoos, bath additives, haircare preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleaning cloths, oils or powders.

The present invention accordingly relates also to a personal care preparation comprising at least one compound of formula (1a), (1b) or (1c) and cosmetically tolerable carriers or adjuvants.

The personal care preparation according to the present invention contains from 0.01 to 15% by weight, preferably from 0.1 to 10% by weight, based on the total weight of the composition, of a compound of formula (1a), (1b) or (1c), and cosmetically tolerable adjuvants.

Depending upon the form of the personal care preparation, it comprises, in addition to the 3-aryl-2-cyano-3-hydroxy-acrylic acid derivatives of formula (1a), (1b) or (1c), further constituents such as, for example, sequestering agents, colorants, perfume oils, thickeners or solidifiers (consistency regulators), emollients, UV-absorbers, skin protective agents, antioxidants, additives that improve the mechanical properties, such as dicarboxylic acids and/or aluminum, zinc, calcium or magnesium salts of $C_{14}$-$C_{22}$ fatty acids, and, optionally, preservatives.

The personal care preparation according to the present invention may be in the form of a water-in-oil or oil-in-water emulsion, an alcoholic or alcohol-containing formulation, a vesicular dispersion of an ionic or non-ionic amphiphilic lipid, a gel, a solid stick or an aerosol formulation.

As a water-in-oil or oil-in-water emulsion, the cosmetically tolerable adjuvant contains preferably from 5 to 50% of an oil phase, from 5 to 20% of an emulsifier and from 30 to 90% water. The oil phase may comprise any oil suitable for cosmetic formulations such as, for example, one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the present invention are used in various fields, especially for example in the following preparations:

skin-care preparations, e.g. skin-washing and cleansing preparations in the form of tablet-form or liquid soaps, synthetic detergents or washing pastes, skin emulsions, multiemulsions or skin oils;

bath preparations, e.g. liquid (foam baths, milks, shower preparations) or solid bath preparations, e.g. bath cubes and bath salts;

cosmetic leave-on personal care preparations, e.g. facial make-up in the form of day creams or powder creams, face powder (loose or pressed), rouge or cream make-up, eye-care preparations, e.g. eyeshadow preparations, mascaras, eyeliners, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams or oils, sun-blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

dental care, denture-care and mouth-care preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

An antimicrobial soap has, for example, the following composition:
0.01 to 5% by weight of a compound of formula (1a), (1b) or (1c),
0.3 to 1% by weight titanium dioxide,
1 to 10% by weight stearic acid,
soap base ad 100%, e.g. a sodium salt of tallow fatty acid or coconut fatty acid, or glycerol.

A shampoo has, for example, the following composition:
0.01 to 5% by weight of a compound of formula (1a), (1b) or (1c),
12.0% by weight sodium laureth-2-sulfate,
4.0% by weight cocamidopropyl betaine,
3.0% by weight NaCl and
water ad 100%.

A deodorant has, for example, the following composition:
0.01 to 5% by weight of a compound of formula (1a), (1b) or (1c),
60% by weight ethanol,
0.3% by weight perfume oil, and
water ad 100%.

The present invention relates also to an oral composition containing from 0.01 to 15% by weight, based on the total weight of the composition, of a compound of formula (1a), (1b) or (1c), and orally tolerable adjuvants.

Example of an oral composition:
10% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer,
0.10% by weight peppermint flavouring,
0.1 to 0.5% by weight of a compound of formula (1a), (1b) or (1c), and
48.6% by weight water.

The oral composition according to the present invention may be, for example, in the form of a gel, a paste, a cream or an aqueous preparation (mouthwash).

The oral composition according to the present invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

3-aryl-2-cyano-3-hydroxy-acrylic acid derivatives of formulae (1a), (1b) or (1c) according to the present invention are also suitable for treating, especially preserving, textile fibre materials. Such materials are undyed and dyed or printed fibre materials, for example made of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

3-aryl-2-cyano-3-hydroxy-acrylic acid derivatives according to the present invention am suitable also for treating, especially imparting antimicrobial properties to or preserving, plastics such as, for example, polyethylene, polypropylene, polyurethane, polyester, polyamide, polycarbonate, latex etc. Fields of use therefor are, for example, floor coverings, plastics coatings, plastics containers and packaging materials; kitchen and bathroom utensils (e.g. brushes, shower curtains, sponges, bathmats), latex, filter materials (air and water filters), plastics articles used in the field of medicine such as, for example, dressing materials, syringes, catheters etc., so-called "medical devices", gloves and mattresses.

Paper, for example papers used for hygiene purposes, may also be provided with antimicrobial properties using the 3-aryl-2-cyano-3-hydroxy-acrylic acid derivatives of formulae (1a), (1b) or (1c) according to the present invention.

It is also possible for nonwovens such as, for example, nappies/diapers, sanitary towels, panty liners, and cloths for hygiene and household uses, to be provided with antimicrobial properties in accordance with the present invention.

The 3-aryl-2-cyano-3-hydroxy-acrylic acid derivatives of formulae (1a), (1b) or (1c) are also used in washing and cleaning formulations such as, for example, liquid or powder washing agents or softeners.

The 3-aryl-2 cyano-3-hydroxy-acrylic add derivatives of formulae (1a), (1b) or (1c) can also be used especially in household and general-purpose cleaners for cleaning and disinfecting hard surfaces.

A cleaning preparation has, for example, the following composition:
0.01 to 5% of a compound of formula (1a), (1b) or (1c),
3.0% octyl alcohol 4EO,
1.3% fatty alcohol $C_6$-$C_{10}$polyglucoside,
3.0% isopropanol, and
water ad 100%.

In addition to preserving cosmetic and household products, the preservation of technical products, the provision of technical products with antimicrobial properties and use as a biocide in technical processes are also possible, for example in paper treatment, especially in paper treatment liquors, printing thickeners of starch or cellulose derivatives, surface-coatings and paints.

The 3-aryl-2-cyano-3-hydroxy-acrylic acid derivatives of formulae (1a), (1b) or (1c) are also suitable for the antimicrobial treatment of wood and for the antimicrobial treatment of leather, the preserving of leather and the provision of leather with antimicrobial properties.

The compounds according to the present invention are also suitable for the protection of cosmetic products and household products from microbial damage.

Furthermore, the compounds of the present invention are able to penetrate biofilms formed on animated and inanimated surfaces. They can also, if necessary, prevent the adhesion of bacteria on surfaces and the further forming of the biofilms. They are able to detach the biofilm and/or to inhibit the growth of the biofilm forming microorganisms in the biological matrix or to kill them.

Generally, biofilms are aggregates of animated or inanimated microorganisms, preferably bacteria, together with their intermediate catabolic products in form of extracellular polymer substances (EPS-matrix), like polysaccharides. The efficacy of antimicrobial actives, which normally show a distinct growth-inhibition or killing activity against plankton cells, may strongly be reduced for microorganisms, which are organized in biofilms, i.e. because of insufficient penetration of the active into the biomatrix.

The compounds of the present invention are therefore effective actives against biofilms which are formed on the surface of teeth and oral mucosa, which are participated in the formation of degenerative an diseases in the oral region, like caries or periodontosis.

The following Examples illustrate, but do not limit, the present invention.

EXAMPLE 1

Preparation of aryl-mono-(2-cyano-3-hydroxy-acrylic acid)-ester (101)

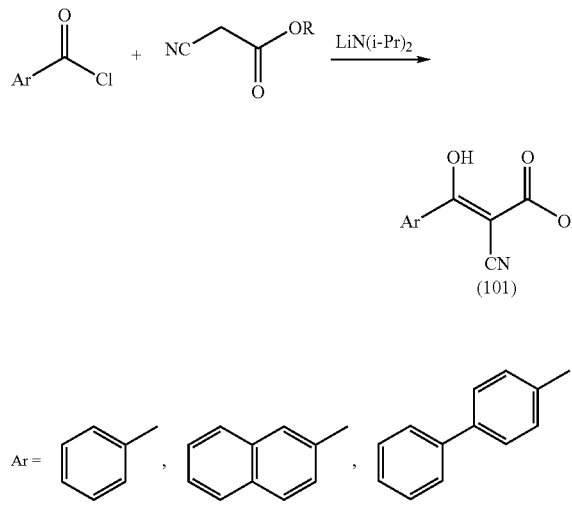

R = iso-butyl, n-butyl, iso-propyl, n-octyl, iso-octyl

A 1.6 m solution of 1 mmol n-BuLi in hexane is added to a solution of 1 mmol diisopropylamine in $THF_{abs}$ (6 ml/ml diisopropylamine) at −10° C. The mixture is stirred for 15 min. and than cooled down to −78° C.

After that the solution of 0.5 mmol of the corresponding cyano acetate is added in THF (1 ml/g cyanoacetate) at this temperature initially, additionally stirred for 15 min and than the solution of 0.5 mmol of the acid chloride is added in THF (2 ml/g acid chloride).

After stirring for 45 min at −78° C. the reaction mixture is quenched at this temperature with 15% HCl und warmed up to room temperature over night.

For working up the reaction mass is extracted with acetic acid ester, the organic phase is washed with water for several times, dried and purified and concentrated.

The product is isolated and purified via chromatographic methods on silica gel (acidic acid ester/hexane 10/1).

The following derivatives are obtained with this method:

|        | Ar          | R        | Yield [%] |
|--------|-------------|----------|-----------|
| (101a) | 4-biphenyl  | i-propyl | 37        |
| (101b) | 4-biphenyl  | n-butyl  | 25        |
| (101c) | 4-biphenyl  | i-butyl  | 18        |
| (101d) | 4-biphenyl  | n-octyl  | 23        |
| (101e) | 4-biphenyl  | i-octyl  | 22        |
| (101f) | 2-naphthyl  | n-octyl  | 20        |

EXAMPLE 2

Preparation of aryl-bis-(2-cyano-3-hydroxy-acrylic acid) ester (102)

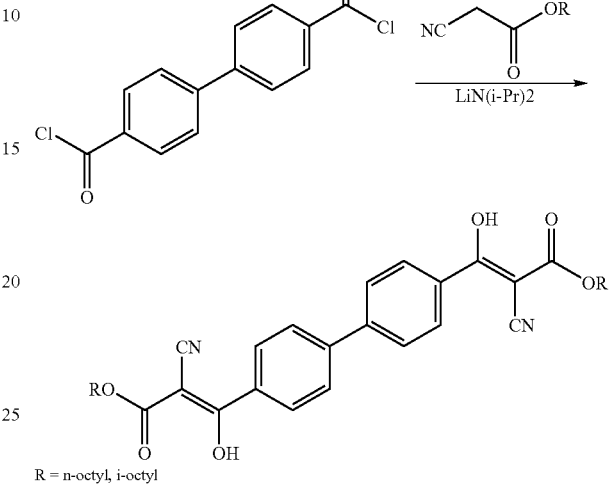

R = n-octyl, i-octyl

A 1.6 m solution mmol of n-BuLi in hexane is added at −10° C. to a solution of 1 mmol diisopropylamine in $THF_{abs}$ (6 ml/ml diisopropylamine). The mixture is stirred for 15 min. and than cooled down to −78° C.

After that the solution of 0.5 mmol of the corresponding cyano acetate is added in THF (1 ml/g cyanoacetate) at this temperature initially, additionally stirred for 15 min and than the solution of 0.5 mmol of the acid chloride is added in THF (2 ml/g acid chloride).

After stirring of 45 min at −78° C. the reaction mixture is quenched at this temperature with 15% HCl und warmed up to room temperature over night.

The working up for reconditioning, isolation and purification is carried out according to example 1.

The following derivatives are obtained with this method:

| Comp. of formula | R       | Yield [%] |
|------------------|---------|-----------|
| (102a)           | n-octyl | 13        |
| (102b)           | i-octyl | 21        |

TABLE 1

1H-NMR data of the compounds:

| Formula | Compound | 1H-NMR (CDCl$_3$) |
|---------|----------|-------------------|
| (101b)  | 3-biphenyl-4-yl-2-cyano-3-hydroxy-acrylic acid butylester | 0.99(3H, t, J=7.43Hz), 1.45-1.49(2H, m), 1.74-1.79(2H, m), 4.36(2H, t, J=6.66Hz), 7.41(1H, t, J=5.89Hz), 7.47(2H, t, J=6.92Hz), 7.62(2H, d, J=6.92Hz), 7.71(2H, d, J=8.71Hz), 8.10(2H, d, J=8.46Hz), 14.27(1H, s) |

TABLE 1-continued

1H-NMR data of the compounds:

| Formula | Compound | 1H-NMR (CDCl$_3$) |
|---|---|---|
| (101c) | 3-biphenyl-4-yl-2-cyano-3-hydroxy-acrylic acid isobutylester | 1.03(6H, d, J=6.66Hz), 2.07-2.12(1H, m), 4.13(2H, d, J=6.66Hz), 7.40(1H, t, J=7.30Hz), 7.47(2H, t, J=7.43Hz), 7.62(2H, d, J=7.42Hz), 7.71(2H, d, J=8.20Hz), 8.10(2H, d, J=8.46Hz), 14.27(1H, s) |
| (101d) | 3-biphenyl-4-yl-2-cyano-3-hydroxy-acrylic acid octylester | 0.89(3H, t, J=6.66Hz), 1.22-1.45(10H, m), 1.79(2H, m), 4.34(2H, t, J=6.66Hz), 7.40(1H, t, J=7.17Hz), 7.47(2H, t, J=7.17Hz), 7.62(2H, d, J=7.17Hz), 7.71(2H, d, J=8.45Hz), 8.09(2H, d, J=8.45Hz), 14.27(1H, s) |
| (101e) | 3-biphenyl-4-yl-2-cyano-3-hydroxy-acrylic acid 2-ethyl-hexylester | 0.85-0.97(6H, m), 1.25-1.45(8H, m), 1.72-1.78(1H, m), 4.24-4.28(2H, m), 7.40(1H, t, J=7.17Hz), 7.46(2H, d, J=7.30Hz), 7.62(2H, d, J=7.17Hz), 7.71(2H, d, J=8.712Hz), 8.09(2H, d, J=8.45Hz), 14.27(1H, s) |
| (102a) | 2-Cyano-3-[4'-(2-cyano-1-hydroxy-2-octyloxycarbonyl-vinyl)-biphenyl-4-yl-3-hydroxy-acrylic acid octyl-ester | 0.87-0.91(6H, t, J=6.92Hz), 1.20-1.45(20H, m), 1.77-1.82(4H, m), 4.35(4H, t, J=6.66Hz), 7.75(4H, d, J=6.92Hz), 8.12(4H, d, J=8.46Hz), 14.27(2H, s) |
| (102b) | 2-Cyano-3-[4'-(2-cyano-2-(2-ethyl-hexyloxycarbonyl)-1-hydroxy-vinyl)-biphenyl-4-yl-3-hydroxy-acrylic acid-2-ethylhexylester | 0.9-0.97(12H, m), 1.30-1.50(16H, m), 1.71-1.78(2H, m), 4.20-4.30(4H, m), 7.75(4H, d, J=8.46Hz), 8.13(4H, d, J=8.46Hz), 14.27(2H, s) |
| (101f) | 2-Cyano-3-hydroxy-3-naphthalen-2-yl-acrylic acid-octyl ester | 0.89(3H, t, J=6.83Hz), 1.20-1.55(10H, m), 1.75-180(2H, m), 4.35(2H, t, J=6.83Hz), 7.50-7.60(2H, m), 7.86(1H, d, J=8.29Hz), 7.91-7.98(3H, m), 8.58(1H, s), 14.27(1H, s) |

TABLE 2

13C-NMR data of the compounds

| Compound | | 13C-NMR (CDCl3) |
|---|---|---|
| (101b) | 3-biphenyl-4-yl-2-cyano-3-hydroxy-acrylic acid-butylester | 13.81, 19.11, 30.49, 66.66, 78.63, 115.90, 127.11, 128.29, 128.86, 129.06, 129.97, 139.33, 145.91, 171.22, 182.11. |
| (101c) | 3-biphenyl-4-yl-2-cyano-3-hydroxy-acrylic acid-isobutylester | 19.06, 27.80, 72.53, 78.62, 115.83, 127.12, 128.30, 128.87, 129.06, 129.99, 139.34, 145.91, 171.18, 182.10 |
| (101d) | 3-biphenyl-4-yl-2-cyano-3-hydroxy-acrylic acid octylester | 14.24, 22.75, 25.80, 25.89, 28.50, 29.23, 31.85, 66.97, 78.65, 115.91, 127.12, 128.30, 128.87, 129.06, 129.98, 139.33, 145.91, 171.24, 182.11. |
| (101e) | 3-biphenyl-4-yl-2-cyano-3-hydroxy-acrylic acid-2-ethyl-hexylester | 11.09, 14.16, 14.25, 22.79, 23.00, 23.69, 28.94, 29.45, 29.78, 30.23, 31.99, 38.69, 69.00, 78.63, 115.71, 127.06, 128.25, 128.81, 129.03, 129.94, 139.27, 145.83, 171.26, 181.95. |
| (102a) | 2-cyano-3-[4'-(2-cyano-1-hydroxy-2-octyloxycarbonyl-vinyl)-biphenyl-4-yl-3-hydroxy-acrylic acid-octylester | 14.25, 22.75, 25.80, 28.49, 29.23, 31.85, 67.08, 79.11, 115.71, 127.33, 129.24, 131.09, 144.05, 171.10, 181.76. |
| (102b) | 2-cyano-3-[4'-(2-cyano-2-(2-ethyl-hexyloxycarbonyl)-1-hydroxy-vinyl)-biphenyl-4-yl-3-hydroxy-acrylic acid-2-ethylhexyl-ester | 11.09, 14.16, 22.99, 23.68, 28.93, 30.21, 38.68, 69.11, 79.10, 115.52, 127.28, 129.20, 131.06, 143.97, 171.12, 181.61. |

EXAMPLE 3

Synthesis of β-aryl-α-cyano-β-ketoester

To a solution of α-cyanoester (1 mmol), MgCl$_2$ (1 mmol) in dry CH$_3$CN (5 mL/g of aroyl chloride), maintained at 0° C. is added NEt$_3$ (2 mmol) and the mixture is stirred for 5 min.

DMAP (0.5 mmol) is added and the mixture is stirred further for 15 min.

To this mixture is then added acid chloride (1 mmol), the reaction mass is stirred at 0° C. for 45 min and a further 1 h at RT.

The reaction mixture is quenched with 15% HCl at 0° C. and extracted with ethyl acetate.

The organic phase is washed with water, brine and dried over Na$_2$SO$_4$.

It is concentrated under reduced pressure and the crude is subjected to column chromatography over silica gel.

Further purification is achieved by a recolumn.

The yields for various β-aryl-α-cyano-β-ketoesters are given in Table 2. $^1$H-NMR and $^{13}$C-NMR data for these derivatives are given in Tables 3 and 4 respectively.

TABLE 2

Synthesis of β-aryl-α-cyano-β-ketoester

| Comp. of formula | Aroyl chloride | Cyano ester | Yield % |
|---|---|---|---|
| (101b) | Biphenyl carbonyl chloride | n-butyl | 70.0 |
| (101d) | Biphenyl carbonyl chloride | n-octyl | 70.0 |
| (101g) | Biphenyl carbonyl chloride | n-decyl | 30.7 |
| (101h) | p-phenoxybenzoyl chloride | n-butyl | 42.0 |
| (101i) | p-phenoxybenzoyl chloride | n-octyl | 50.0 |
| (101k) | p-phenoxybenzoyl chloride | i-octyl | 45.0 |
| (101l) | p-phenoxybenzoyl chloride | n-decyl | 38.0 |
| (101m) | 4-toluoyl chloride | n-butyl | 76.5 |
| (101n) | 4-toluoyl chloride | n-octyl | 62.4 |
| (101o) | 4-toluoyl chloride | n-decyl | 81.6 |

TABLE 3

1H NMR spectral data

| Comp. of formula | Compound | 1H NMR data |
|---|---|---|
| (101b) | *3-Biphenyl-4-yl-2-cyano-3-hydroxy-acrylic acid butyl ester | 0.99(3H, t, J=7.43Hz), 1.45-1.49(2H, m), 1.74-1.79(2H, m), 4.36(2H, t, J=6.66Hz), 7.41(1H, t, J=5.89Hz), 7.47(2H, t, J=6.92Hz), 7.62(2H, d, J=6.92Hz), 7.71(2H, d, J=8.71Hz), 8.10(2H, d, J=8.46Hz), 14.27(1H, s) |
| (101d) | *3-Biphenyl-4-yl-2-cyano-3-hydroxy-acrylic acid octyl ester | 0.89(3H, t, J=6.66Hz), 1.22-1.45(10H, m), 1.79(2H, m), 4.34(2H, t, J=6.66Hz), 7.40(1H, t, J=7.17Hz), 7.47(2H, t, J=7.17Hz), 7.62(2H, d, J=7.17Hz), 7.71(2H, d, J=8.45Hz), 8.09(2H, d, J=8.45Hz), 14.27(1H, s) |
| (101g) | 3-Biphenyl-4-yl-2-cyano-3-hydroxy-acrylic acid decyl ester | 0.89(3H, t, J=5.61Hz), 1.28-1.55(14H, m), 1.79(2H, m), 4.36(2H, t, J=6.83Hz), 7.42(1H, t, J=6.80Hz), 7.48(2H, t, J=6.80Hz), 7.63(2H, d, J=7.80Hz), 7.73(2H, d, J=7.80Hz), 8.12(2H, d, J=8.29Hz), 14.27(1H, s) |
| (101h) | 2-Cyano-3-hydroxy-3-(4-phenoxy-phenyl)-acrylic acid butyl ester | 0.98(3H, t, J=7.31Hz), 1.44-1.48(2H, m), 1.72-1.79(2H, m), 4.34(2H, t, J=6.83Hz), 7.04(2H, d, J=8.29Hz), 7.09(2H, d, J=8.29Hz), 7.22(1H, t, J=7.31Hz), 7.41(2H, t, J=7.56Hz), 8.04(2H, d, J=8.78Hz), 14.27(1H, s) |
| (101i) | 2-Cyano-3-hydroxy-3-(4-phenoxy-phenyl)-acrylic acid octyl ester | 0.88(3H, t, J=6.83Hz), 1.29-1.54(10H, m), 1.75-1.79(2H, m), 4.33(2H, t, J=6.83Hz), 7.04(2H, d, J=9.26Hz), 7.09(2H, d, J=7.8Hz), 7.22(1H, t, J=7.56Hz), 7.41(2H, t, J=8.04Hz), 8.04(2H, d, J=8.78Hz), 14.27(1H, s) |
| (101k) | 2-Cyano-3-hydroxy-3-(4-phenoxy-phenyl)-acrylic acid 2-ethyl-hexyl ester | 0.90-0.96(6H, m), 1.29-1.49(8H, m), 1.71-1.74(1H, m), 4.24-4.28(2H, m), 7.04(2H, d, J=8.78Hz), 7.09(2H, d, J=7.31Hz), 7.22(1H, t, J=7.56Hz), 7.41(2H, t, J=8.04Hz), 8.04(2H, d, J=8.78Hz), 14.27(1H, s) |
| (101l) | 2-Cyano-3-hydroxy-3-(4-phenoxy-phenyl)-acrylic acid decyl ester | 0.88(3H, t, J=6.83Hz), 1.28-1.54(14H, m), 1.75-1.78(2H, m) 4.33(2H, t, J=6.83Hz), 7.04(2H, d, J=8.78Hz), 7.09(2H, d, J=7.31Hz), 7.22(1H, t, J=7.51Hz), 7.41(2H, t, J=7.80Hz), 8.04(2H, d, J=8.78Hz), 14.27(1H, s) |
| (101m) | 2-cyano-3-hydroxy-3-p-tolyl-acrylic acid butyl ester | 0.89(3H, t, J=7.31Hz), 1.34-1.43(2H, m), 1.64-1.71(2H, m), 2.34(3H, s), 4.26(2H, t, J=6.58Hz), 7.22(2H, d, J=8.29Hz), 7.85(2H, d, J=8.29Hz), 14.27(1H, s) |
| (101n) | 2-cyano-3-hydroxy-3-p-tolyl-acrylic acid octyl ester | 0.89(3H, t, J=6.83Hz), 1.28-1.42(10H, m), 1.73-1.78(2H, m), 2.42(3H, s), 4.33(2H, t, J=6.83Hz), 7.30(2H, d, J=7.8Hz), 7.93(2H, d, J=8.29Hz), 14.27(1H, s) |
| (101o) | 2-cyano-3-hydroxy-3-p-tolyl-acrylic acid decyl ester | 0.81(3H, t, J=6.83Hz), 1.20-1.35(14H, m), 1.65-1.72(2H, m), 2.42(3H, s), 4.25(2H, t, J=6.83Hz), 7.22(2H, d, J=7.8Hz), 7.85(2H, d, J=8.29Hz), 14.27(1H, s) |

TABLE 4

13C spectral data

| Comp. of formula | Compound | 13C data |
|---|---|---|
| (101b) | *3-biphenyl-4-yl-2-cyano-3-hydroxy-acrylic acid butylester | 13.81, 19.11, 30.49, 66.66, 78.63, 115.90, 127.11, 128.29, 128.86, 129.06, 129.97, 139.33, 145.91, 171.22, 182.11. |
| (101d) | *3-biphenyl-4-yl-2-cyano-3-hydroxy-acrylic acid octyl ester | 14.24, 22.75, 25.80, 25.89, 28.50, 29.23, 31.85, 66.97, 78.65, 115.91, 127.12, 128.30, 128.87, 129.06, 129.98, 139.33, 145.91, 171.24, 182.11. |
| (101g) | 3-biphenyl-4-yl-2-cyano-3-hydroxy-acrylic acid decyl-ester | 14.07, 22.66, 25.70, 28.42, 29.16, 29.27, 29.45, 29.49, 31.86, 66.95, 78.65, 115.94, 127.26, 128.43, 129.00, 129.22, 130.19, 139.56, 146.14, 171.60, 182.38. |
| (101h) | 2-Cyano-3-hydroxy-3-(4-phenoxy-phenyl)-acrylic acid butyl ester | 13.61, 18.97, 30.44, 66.54, 78.65, 116.04, 117.27, 120.43, 124.93, 125.40, 130.13, 130.94, 155.44, 162.60, 171.70, 181.9.4 |
| (101i) | 2-Cyano-3-hydroxy-3-(4-phenoxy-phenyl)-acrylic acid octyl ester | 14.03, 22.59, 25.68, 28.41, 29.09, 31.73, 66.85, 77.79, 116.18, 117.27, 120.41, 124.93, 125.40, 130.12, 130.93, 155.08, 162.33, 171.66, 181.89. |
| (101k) | 2-Cyano-3-hydroxy-3-(4-phenoxy-phenyl)-acrylic acid 2-ethyl-hexyl ester | 10.95, 13.99, 22.88, 23.66, 28.88, 30.20, 38.71, 69.01, 77.79, 116.03, 117.28, 120.42, 124.92, 125.32, 130.13, 130.94, 155.10, 162.33, 171.73, 181.79. |
| (101l) | 2-Cyano-3-hydroxy-3-(4-phenoxy-phenyl)-acrylic acid decyl ester | 14.03, 22.59, 25.68, 28.41, 29.10, 29.21, 29.39, 29.45, 31.73, 66.85, 77.79, 116.03, 117.28, 120.42, 124.92, 130.95, 130.94, 155.10, 162.33, 171.73, 181.79. |
| (101m) | 2-cyano-3-hydroxy-3-p-tolyl-acrylic acid butyl ester | 13.57, 18.93, 21.66, 30.39, 66.47, 78.12, 115.98, 128.63, 128.70, 129.33, 144.33, 171.55, 182.83. |
| (101n) | 2-cyano-3-hydroxy-3-p-tolyl-acrylic acid octyl ester | 13.94, 21.58, 22.51, 25.60, 28.31, 29.00, 31.64, 66.72, 78.18, 115.89, 128.58, 128.64, 129.26, 144.26, 171.50, 182.72. |
| (101o) | 2-cyano-3-hydroxy-3-p-tolyl-acrylic acid decyl ester | 14.02, 21.64, 22.60, 25.64, 28.37, 29.10, 29.22, 29.39, 29.45, 31.81, 66.77, 78.24, 115.96, 128.63, 128.70, 129.31, 144.31, 171.55, 182.80. |

EXAMPLE 4

Determination of the Minimum Inhibitory Concentration (MIC Value)

a) Automatic MIC-Screening according to the broth dilution method:

Medium: Casein/soymeal peptone agar (Merck)
Diluent: DMSO
Microorganisms used:
  *Staphylococcus aureus* ATCC 6538
  *Escherichia coli* ATCC 10536
  *Actinomyces viscosus* ATCC 43146
  *Corynebacterium xerosis* ATCC 373 oder
  *C. minutissimum* ATCC 23348
Incubation: 24 to 48 hours at 37° C.
Test solution: 0.3% stock solutions of all the test substances are prepared in a suitable solvent and diluted in serial dilutions to end concentrations of 120 µg/ml to 3.75 µg/ml in DSMO in Deep-Well-plates.

Test Principle:

8 µl of each dilution step is mixed with 192 µl of nutrient medium in micro titer plates. The plates are incubated at 37° C. for 24 hours and then the highest dilution (lowest concentration) of the test substance at which growth is just no longer discernible is determined (corresponds to the MIC).

*Actinomyces viscosus* ATCC43146
*Fusobacterium nucleatum* subsp. polymorphum ATCC1095
*Porphyromonas gingivalis* ATCC3277
*Prevotella nigrescens* ATCC33563

Incubation: 7-10 days at 37° C. under anaerobic conditions, resp. 24 h aerobically with 10% $CO_2$ for Streptococci und *A. actinomycetemcomitans*

TABLE 4

MIK in [µγ/ml]

| Comp. of formula | Structure | S. aureus | Corynebacterium sp. | A. viscosus |
|---|---|---|---|---|
| (101b) | | 7.5 | 15 | 7.5 |
| (101c) | | 7.5 | 7.5 | 7.5 |
| (101d) | | <3.75 | <3.75 | <3.75 |
| (102a) | | <3.75 | >120 | <3.75 | b) Determination of MIC vs. different oral germs in the broth dilution method

Medium: Thioglycolate Bouillon with Hemin and Menadion Columbia Bouillon with Hemin and Menadion für *P. gingivalis* und *P. nigrescens* diluent: the corresponding amount of the substances was pippeted directly

Examples of Test organisms:
*Actinobacillus actinomycetemcomitans* ATCC43718
*Streptococcus gordonii* ATCC10558
*Streptococcus mutans* ATCC33402

Test solution: Stock solutions in ethanol with 1500 ppm (w/w) are used from all test substances Test Principle:

Bacteria are taken from blood agar plates with cotton swabs and a suitable O.D. is adjusted in the corresponding medium (McFarland 0.5). This solution is used for *F. nucleatum* and *P. nigrescens* in undiluted state, for the other strains a dilution of 1:20 is used. To each 2 ml of active ingredient containing solution 0.1 ml of the bacteria culture is added and incubated as described above.

The results are listed in Table 5.

TABLE 5

| | MHK in [ppm] | | | | | |
|---|---|---|---|---|---|---|
| | (101b) | (101c) | (101d) | (101e) | (201a) | (201b) |
| *A. actinomycetemcomitans* ATCC43718 | 15 | 15 | ≧15 | >15 | >15 | >15 |
| *S. gordonii* ATCC10558 | 3.75 | 3.75 | ≦0.94 | <0.94 | 15 | 15 |
| *S. mutans* ATCC33402 | 5.63 | 5.63 | ≦0.94 | <0.94 | >15 | >15 |
| *A. viscosus* ATCC43146 | 3.75 | 7.5 | ≦0.94 | <0.94 | 7.5 | 7.5 |
| *F. nucleatum* subsp. *polymorphum* ATCC10953 | ≦0.94 | 7.5 | 15 | >15 | ≧15 | >15 |
| *P. gingivalis* ATCC3277 | 3.75 | 7.5 | 7.5 | 15 | >15 | >15 |
| *P. nigrescens* ATCC33563 | >15 | >15 | >15 | >15 | >15 | >15 | c) Determination of MIC for an extended germ spectrum in the Agar incorporation test Medium:
Casein/soymeal peptone agar (Merck)
*Sabouraud 4% glucose agar (Merck)
Diluent: Sterile 0.85% NaCl solution
Microorganisms used (examples):
*Staphylococcus aureus* ATCC 6538
*Staphylococcus epidermidis* ATCC 12228
*Corynebacterium xerosis* ATCC 373
*Propionibacterium acnes* ATCC 6919
*Escherichia coil* ATCC 10536
*Pseudomonas aeruginosa* ATCC 15442
*Candida albicans* ATCC 10231*
Incubation:
24 hours at 37° C.
*=3 days at 28° C.
Test solution: 1% stock solutions of all the test substances are prepared in a suitable solvent and diluted in serial dilutions to end concentrations of from 1000 ppm to 10 ppm.

Test Principle:
0.3 ml of each dilution step is mixed with 15 ml of nutrient medium while the latter is still liquid. After the nutrient medium has solidified, 10 μl of each of the following organism dilutions of the test strains in 0.85% NaCl solution are spotted onto the agar medium.

The plates are incubated during 24 hours at 37° C. and then the highest dilution (lowest concentration) of the test substance at which growth is just no longer discernible (corresponds to the MIC) is determined.

TABLE 6

| | MIC [in ppm] | | | | |
|---|---|---|---|---|---|
| | Compound of formula | | | | |
| | (101b) | (101c) | (101d) | (101e) | (201b) |
| *Staphylococcus aureus* ATCC 6538 | 6.25 | 12.5 | <1.56 | 1.9 | 100 |
| *Staphylococcus epidermidis* ATCC 12228 | 6.25 | 6.25 | <1.56 | 1.9 | 25 |
| *Corynebacterium xerosis* ATCC 373 | 3.13 | 3.13 | <1.56 | 1.9 | <1.56 |
| *C. minutissimum* ATCC 23348 | 12.5 | 12.5 | <1.56 | | 50 |

TABLE 6-continued

| | MIC [in ppm] | | | | |
|---|---|---|---|---|---|
| | Compound of formula | | | | |
| | (101b) | (101c) | (101d) | (101e) | (201b) |
| *Propionibacterium acnes* ATCC 6919 | 12.5 | 12.5 | 6.25 | 0.94 | <1.56 |
| *Escherischia coli* ATCC 10536 | >100 | >50 | >400 | >500 | >400 |
| *Proteus vulgaris* ATCC 6896 | >100 | >50 | >400 | | >400 |
| *Klebsiella pneumoniae* ATCC 4352 | >100 | >50 | >400 | | >400 |
| *Salmonella choleraesuis* ATCC 9184 | >100 | >50 | >400 | | >400 |
| *Pseudomonas aeruginosa* ATCC 15442 | >100 | >50 | >400 | >500 | >400 |
| *Candida albicans* ATCC 10231 | >100 | >50 | >400 | >500 | >400 |
| *Aspergillus niger* ATCC 6275 | >100 | >50 | >400 | | >400 |

The invention claimed is:

1. Compounds of formula

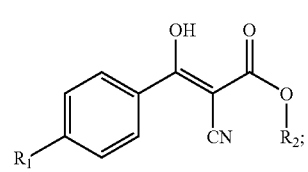

(1a)

wherein $R_1$ is $C_6$-$C_{10}$aryl; or a group of formula (1$a_1$)

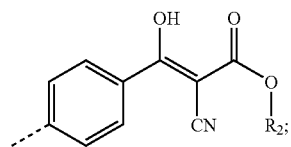

and

R$_2$ is hydrogen; or C$_1$-C$_{20}$alkyl.

2. Compounds of formula (1a) according to claim 1, wherein
R$_1$ is C$_6$-C$_{10}$aryl.

3. Compounds according to claim 1, wherein
R$_1$ is phenyl.

4. Compounds according to claim 1, wherein
R$_2$ is C$_1$-C$_{20}$alkyl.

5. Compounds according to claim 1, which correspond to formula (2)

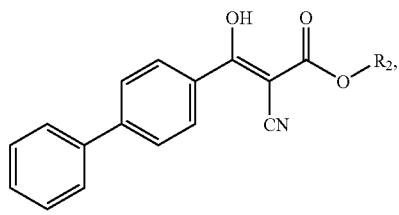

wherein
R$_2$ is C$_1$-C$_{20}$alkyl.

6. Compounds according to claim 1, which correspond to formula (3)

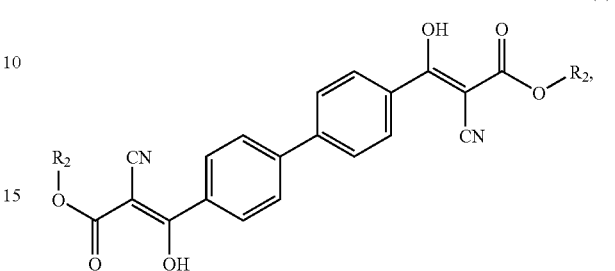

wherein
R$_2$ is C$_1$-C$_{20}$alkyl.

7. A cosmetic composition comprising from 0.01 to 15% by weight, based on the total weight of the composition, of a compound of formula (1a) according to claim 1, and cosmetically tolerable adjuvants.

8. An oral composition comprising from 0.01 to 15% by weight, based on the total weight of the composition, of a compound of formula (1a) according claim 1, and orally tolerable adjuvants.

* * * * *